(12) United States Patent
Stelzer et al.

(10) Patent No.: US 6,387,692 B1
(45) Date of Patent: *May 14, 2002

(54) PROCESS FOR THE PREPARATION OF OPTICALLY ACTIVE AMINES

(75) Inventors: Uwe Stelzer, Burscheid; Claus Dreisbach, Köln, both of (DE)

(73) Assignee: Bayer Aktiengesellschaft, Leverkusen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/077,581

(22) PCT Filed: Nov. 25, 1996

(86) PCT No.: PCT/EP96/05188

§ 371 Date: Jun. 1, 1998

§ 102(e) Date: Jun. 1, 1998

(87) PCT Pub. No.: WO97/20946

PCT Pub. Date: Jun. 12, 1997

(30) Foreign Application Priority Data

Dec. 6, 1995 (DE) .......................................... 195 45 466
Sep. 13, 1996 (DE) .......................................... 196 37 336

(51) Int. Cl.[7] ............................................... C12P 41/00
(52) U.S. Cl. ...................................................... 435/280
(58) Field of Search ........................................ 435/280

(56) References Cited

U.S. PATENT DOCUMENTS 6,187,582 B1 * 2/2001 Stelzer ....................... 435/280

FOREIGN PATENT DOCUMENTS

| DE | 4332738 | | 3/1995 |
| DE | 195 23 151 | | 8/1996 |
| DE | 195 34 208 | | 3/1997 |
| WO | 95/08636 | * | 3/1995 |
| WO | 96/23894 | * | 8/1996 |

OTHER PUBLICATIONS

Ohrner et al., "Kinetic Resolutions of amine and thiol analogues of secondary alcohols catlayzed by the Candida antarctica lipase B", Enzyme and Microbial Tech. 19 : 328–331 (Oct. 1996).*

Pozo et al., "Chiral carbamates through an enzymatic alkoxycarbonylation reaction", Tetrahedron 49 (20) : 4321–26 (1993).*

Chimia, Bd. 48, Nr. 12, Dec. 1994, p. 570, Manfred T. Reetz, et al. "Highly efficient lipase–catalyzed . . . amines".

Abstract of DE 195 34 208, Mar. 20, 1997.

* cited by examiner

Primary Examiner—Sandra Saucier
(74) Attorney, Agent, or Firm—Norris McLaughlin & Marcus

(57) ABSTRACT

Process for preparing optically (S) and (R) active amines of the formula (I*)

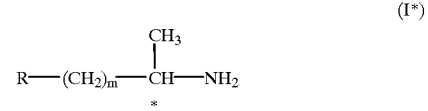

(I*)

comprising reacting racemic amines corresponding to formula (I*) with esters of the formula:

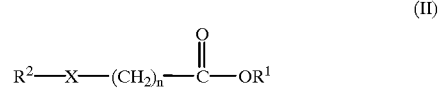

(II)

in the presence of lipase from *Candida antarctica*, and separating the (S)-amine directly from the resulting mixture, and separating the (R)-amine indirectly from the resulting mixture by reacting the acylated (R)-amine therein, which has the formula:

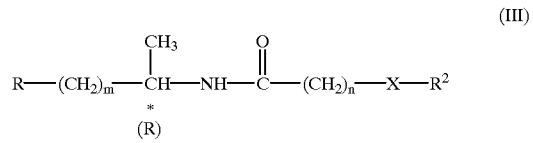

(III)

with acid or base, wherein all the formula above, the variables are as defined herein. Certain precursors of the formula (III) are also disclosed.

4 Claims, No Drawings

PROCESS FOR THE PREPARATION OF OPTICALLY ACTIVE AMINES

This application is a 371 of PCT/EP96/05188, which was filed on Nov. 25, 1996.

The present invention relates to a novel process for preparing known, optically active amines which can be employed as intermediates for preparing pharmaceuticals and crop protection agents. Moreover, the invention relates to novel optically active acylated amines.

It is already known from DE-A 4 332 738 that optically active, primary and secondary amines can be prepared by initially enantioselectively acylating racemic amine in the presence of a hydrolase using an ester which has an electron-rich heteroatom in the acid moiety in the vicinity of the carbonyl carbon atom, then separating the resulting mixture of optically active (S)-amine and optically active acylated (R)-amine (=amide), thereby affording the (S)-amine, and obtaining the other enantiomer, if desired, from the acylated (R)amine by amide cleavage. Suitable hydrolases are lipases from Pseudomonas, for example Amano P, or from Pseudomonas spec. DSM 8246. The degree of optical purity of the enantiomers that are obtained is very high. However, this process has the disadvantages that relatively long reaction times are required for the enzymatic acylation and that the reaction is carried out in highly dilute solution. Only after relatively long reaction times is the remaining (S)-enantiomer obtained in sufficiently high optical yield. For practical purposes, the space-time yields that can be achieved are therefore inadequate. It is a further disadvantage that relatively high amounts of enzyme are required with respect to the substrate. Besides, the enzyme has very high activity, so that purification, concentration and work-up requires considerable effort.

Furthermore, Chimica 48, 570 (1994) discloses that racemic amines will react enantioselectively with ethyl acetate in the presence of lipase from *Candida antarctica* to give mixtures of (S)-amine and acetylated (R)-amine (=amide) from which (S)-amine and acetylated (R)-amine can be isolated, it being possible to set free the acetylated (R)-amine by subsequent amide cleavage. Disadvantages of this method are that once more relatively long reaction times are required and that furthermore the yields are not always satisfactory. In addition, the ratio of enzyme to substrate is again so disadvantageous that an economical utilization of the process is scarcely possible.

It has now been found that optically active amines of the formula

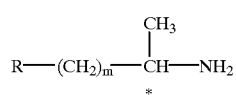

(I*)

in which
R represents aryl which is optionally mono- to trisubstituted by identical or different substituents, but where the positions of the aryl group which are adjacent to the linking point do not carry any substituents, or
represents optionally benzo-fused heteroaryl which is optionally mono- to trisubstituted by identical or different substituents, but where the positions of the heteroaryl group which are adjacent to the linking point do not carry any substituents, or
represents alkyl having 1 to 7 carbon atoms, halogenoalkyl having 1 to 7 carbon atoms and 1 to 5 halogen atoms or alkoxyalkyl having 1 to 7 carbon atoms in the alkyl moiety and 1 to 3 carbon atoms in the alkoxy moiety, and
m represents the numbers 0, 1, 2 or 3,
are obtained by
a) reacting, in a first step, racemic amines of the formula

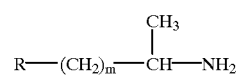

(I)

in which
R and m are each as defined above,
with esters of the formula

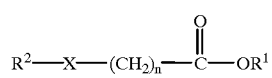

(II)

in which
$R^1$ represents alkyl having 1 to 10 carbon atoms or represents halogenoalkyl having 1 to 6 carbon atoms and 1 to 5 halogen atoms,
$R^2$ represents hydrogen, alkyl having 1 to 10 carbon atoms, halogenoalkyl having 1 to 6 carbon atoms and 1 to 5 halogen atoms or represents phenyl which is optionally mono- to trisubstituted by identical or different substituents from the group consisting of halogen, amino, hydroxyl, alkyl having 1 to 4 carbon atoms, alkoxy having 1 to 4 carbon atoms, phenyl and phenoxy,
X represents oxygen, sulphur or an $-NR^3-$ group in which
$R^3$ represents alkyl having 1 to 4 carbon atoms, and
n represents the numbers 0, 1, 2 or 3,
in the presence of lipase from Candida antarctica and, if appropriate, in the presence of a diluent,
b) separating, in a second step, the resulting mixture of (S)-amine of the formula

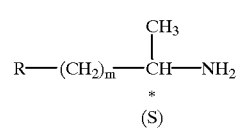

(I-S)

in which
R and m are each as defined above,
and acylated (R)-amine of the formula

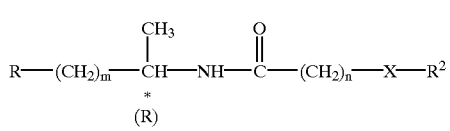

(III)

in which
R, $R^2$, X, m and n are each as defined above, and
c) if appropriate, setting free, in a third step, the (R)-amine of the formula

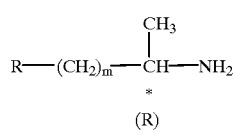

(I-R)

in which
R and m are each as defined above,
from the acylated (R)-amine of the formula (III) by treatment with acid or base, if appropriate in the presence of a diluent.

(R)-amines are understood to mean those optically active compounds of the formula (I) which exhibit the (R) configuration at the asymmetrically substituted carbon atom. Correspondingly, (S)-amines are understood to mean those optically active compounds of the formula (I) which exhibit the (S) configuration at the chiral centre. In the formulae, the asymmetrically substituted carbon atom is in each case indicated by (*).

It is extremely surprising that optically active amines of the formula (I*) can be prepared in high yield and very good optical purity by the process according to the invention. From the known prior art, it could not be foreseen that the specific use of lipase from Candida antarctica effects a high enantioselectivity and a faster reaction in the reaction between amine and ester than the enzyme systems used hitherto in similar processes.

The process according to the invention enjoys a number of advantages. Thus, it makes possible the preparation of a large number of optically active amines in high yield and excellent optical purity. It is also favourable that the reaction can be carried out at relatively high substrate concentration and that the reaction times are short. It is therefore possible to achieve space-time yields which are satisfactory even for practical purposes. It is a further advantage that the biocatalyst required is available in relatively large amounts and that it is stable even at elevated temperatures. In terms of the amount of enzyme relative to the substrate, the biocatalyst is employed in a relatively low amount and low enzyme activity. Finally, no difficulties are involved in carrying out the reaction and isolating the desired substances, namely either the (S)- or the (R)-amines.

If racemic 1-(4-chlorophenyl)-ethylamine is reacted with methyl methoxyacetate in the presence of lipase from Candida antarctica, the resulting components are separated and the (R)-enantiomer of N-[1-(4-chlorophenyl)ethyl]-methoxyacetamide is treated with hydrochloric acid, the course of the process according to the invention can be illustrated by the equation that follows.

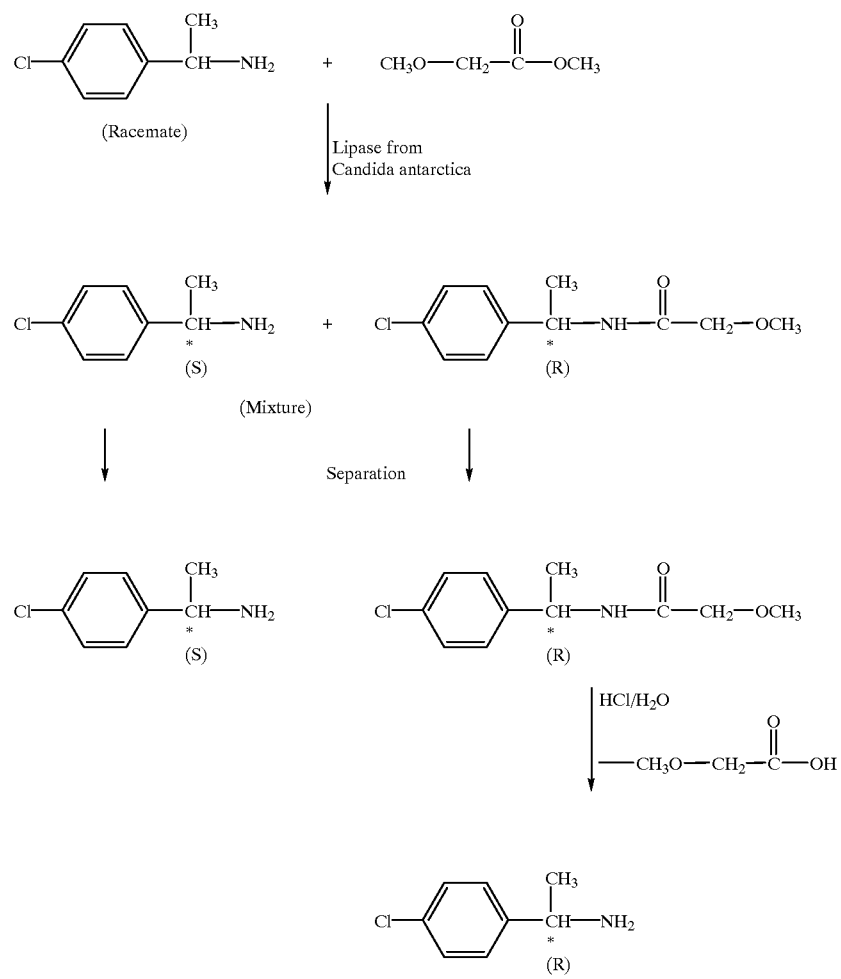

The formula (I) provides a general definition of the racemic amines required as starting materials for carrying out the process according to the invention.

R preferably represents optionally substituted phenyl of the formula

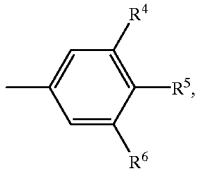

in which

R⁴, R⁵ and R⁶ independently of one another each represent hydrogen, halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, cyano, dialkylamino having 1 to 4 carbon atoms in each alkyl group, nitro, phenyl, phenoxy or benzyl, or R represents naphthyl which is optionally mono- to trisubstituted by identical or different substituents from the group consisting of halogen, alkyl having 1 to 4 carbon atoms, halogenoalkyl having 1 to 4 carbon and 1 to 5 identical or different halogen atoms, alkoxy having 1 to 4 carbon atoms and halogenoalkoxy having 1 to 4 carbon atoms and 1 to 5 identical or different halogen atoms, but where the positions ortho to the carbon atom through which the naphthyl radical is bonded are unsubstituted, or R represents optionally benzo-fused heteroaryl having 5 or 6 ring members and 1 to 3 heteroatoms, such as nitrogen, oxygen and/or sulphur, in the heterocycle, where these radicals may be mono- to trisubstituted by identical or different substituents from the group consisting of halogen, alkyl having 1 to 4 carbon atoms, alkoxy having 1 to 4 carbon atoms and halogenoalkyl having 1 to 4 carbon atoms, but where the positions of the heteroaryl group which are adjacent to the linking point do not carry any substituents, or represents straight-chain or branched alkyl having 1 to 7 carbon atoms, halogenoalkyl having 1 to 5 carbon atoms and 1 to 5 fluorine and/or chlorine atoms or represents alkoxyalkyl having 1 to 5 carbon atoms in the alkyl moiety and, 1 to 3 carbon atoms in the alkoxy moiety.

m also preferably represents the numbers 0, 1, 2 or 3.

Particular preference is given to amines of the formula (I) in which

R represents optionally substituted phenyl of the formula

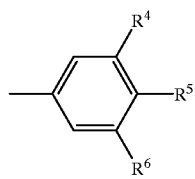

in which

R⁴, R⁵ and R⁶ independently of one another each represent hydrogen, fluorine, chlorine, bromine, methyl, ethyl, n-propyl, isopropyl, n-butyl, iso-butyl, sec-butyl, methoxy, ethoxy, methylthio, trichloromethyl, trifluoromethyl, difluoromethyl, trifluoromethoxy, difluorochloromethoxy, difluoromethoxy, cyano, dimethylamino, diethylamino, nitro, phenyl, phenoxy or benzyl, or R represents naphthyl which is optionally mono- to trisubstituted by identical or different substituents from the group consisting of fluorine, chlorine, bromine, methyl, ethyl, n-propyl, isopropyl, n-butyl, iso-butyl, sec-butyl, methoxy, ethoxy, trichloromethyl, trifluoromethyl, difluoromethyl, trifluoromethoxy, difluorochloromethoxy and difluoromethoxy, but where the positions ortho to the carbon atom through which the naphthyl radical is bonded are not substituted, or R represents optionally benzo-fused furyl, thienyl, pyridyl or pyrimidine, where these radicals may be mono- to trisubstituted by identical or different substituents from the group consisting of fluorine, chlorine, bromine, methyl, ethyl, n-propyl, isopropyl, n-butyl, iso-butyl, sec-butyl, tert-butyl, methoxy, ethoxy, n-propoxy, isopropoxy, trifluoromethyl and trifluoroethyl, but where the positions of the heteroaryl group which are adjacent to the linking point do not carry any substituents, or R represents straight-chain or branched alkyl having 1 to 5 carbon atoms, halogenoalkyl having 1 to 5 carbon atoms and 1 to 3 fluorine and/or chlorine atoms or represents alkoxyalkyl having 1 to 3 carbon atoms in the alkyl moiety and 1 to 3 carbon atoms in the alkoxy moiety and m represents the numbers 0, 1 or 2.

Examples of amines of the formula (I) include the compounds of the formulae that follow:

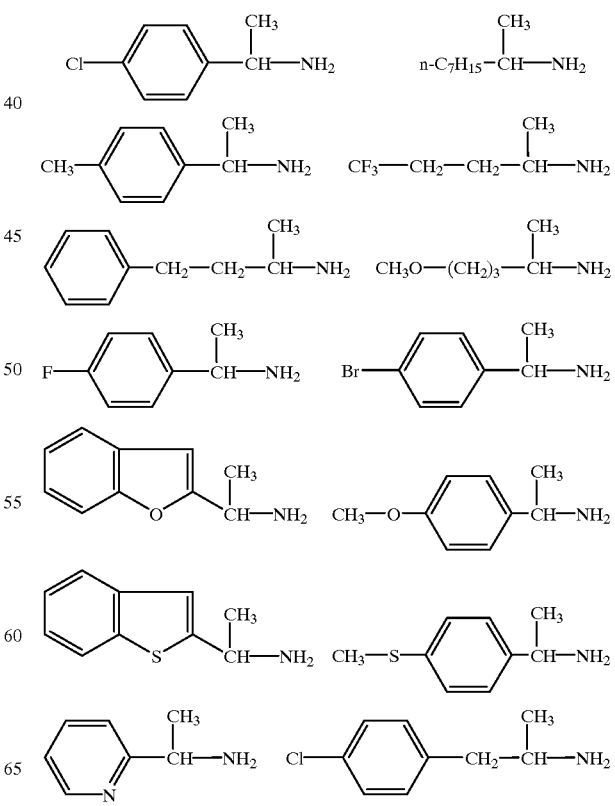

-continued

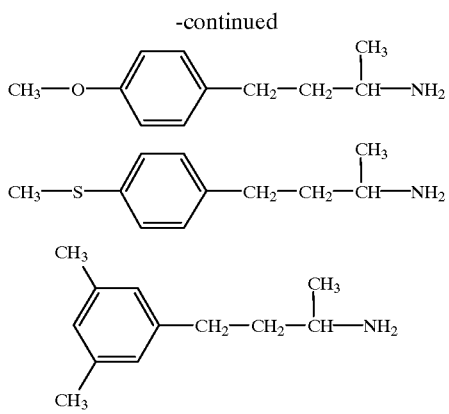

The racemic amines of the formula (I) are known or can be prepared by known methods.

The formula (II) provides a general definition of the esters required as reaction components for carrying out the first step of the process according to the invention.

$R^1$ preferably represents straight-chain alkyl having 1 to 8 carbon atoms or represents straight-chain halogenoalkyl having 1 to 4 carbon atoms and 1 to 3 fluorine and/or chlorine atoms, $R^2$ preferably represents hydrogen, straight-chain alkyl having 1 to 8 carbon atoms, straight-chain halogenoalkyl having 1 to 4 carbon atoms and 1 to 3 fluorine, chlorine and/or bromine atoms, or represents phenyl which is optionally mono- to trisubstituted by identical or different substituents from the group consisting of fluorine, chlorine, bromine, amino, hydroxyl, methyl, ethyl, methoxy, ethoxy, phenyl and phenoxy.

X preferably represents oxygen or sulphur.

n preferably represents the numbers 0, 1 or 2.

Particular preference is given to esters of the formula (II) in which $R^1$ represents methyl, ethyl, n-propyl, n-butyl, chloromethyl, 2-chloroethyl, 2-fluoroethyl or 2,2,2-trifluoroethyl, $R^2$ represents hydrogen, methyl, ethyl, n-propyl, n-butyl, chloromethyl, trifluoromethyl, 2-chloroethyl or represents phenyl which is optionally mono- or disubstituted by fluorine, chlorine, bromine, amino, hydroxyl, methyl, ethyl, methoxy, phenyl and/or phenoxy, X represents oxygen or sulphur and n represents the numbers 1 or 2.

Examples of esters of the formula (II) include the compounds of the formulae that follow.

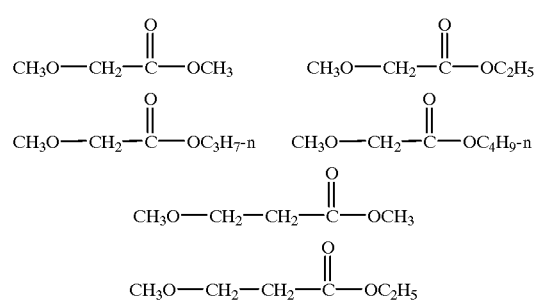

The esters of the formula (II) are known or can be prepared by known methods.

The biocatalyst used for carrying out the first step of the process according to the invention is lipase from Candida antarctica. Preference is given to using the product which is commercially available under the name Novozym 435®.

The lipase can be employed either in native or in modified form, for example microencapsulated or bound to inorganic or organic support materials. Examples of support materials which are suitable in this context are Celite, Lewatit, zeolites, polysaccharides, polyamides and polystyrene resins.

Suitable diluents for carrying out the first step of the process according to the invention are all organic solvents which are customary for such reactions. Preference is given to using ethers, such as methyl tert-butyl ether or tert-amyl methyl ether, furthermore aliphatic or aromatic hydrocarbons, such as hexane, cyclohexane or toluene, additionally nitriles, such as acetonitrile or butyronitrile, moreover alcohols, such as tert-butanol or 3-methyl-3-pentanol, and finally also the esters used for the acylation.

When carrying out the first step of the process according to the invention, the temperatures can be varied within a certain range. In general, the reaction is carried out at temperatures between 0° C. and 80° C., preferably between 10° C. and 60° C.

The first step of the process according to the invention is generally carried out under atmospheric pressure, if appropriate under an inert gas such as nitrogen or argon.

When carrying out the first step of the process according to the invention, generally 0.6 to 10 mol, preferably 1 to 3 mol of ester of the formula (II) are employed per mole of racemic amine of the formula (I). The amount of lipase can also be varied within a certain range. In general, 1 to 10% by weight of immobilized lipase, based on racemic amine, are employed, corresponding to an activity of 10,000 to. 112,000 units of lipase per mole of racemic amine. Specifically, the first step of the process according to the invention is carried out in such a manner that the components are added in any order and the resulting mixture is stirred at the particular reaction temperature until the desired conversion has been achieved. To terminate the reaction, the biocatalyst is generally removed by filtration.

In the second step, the mixture obtained in the first step of the process according to the invention is worked up by customary methods. Generally, the desired components are isolated by distillation, fractional crystallization, acid-base solvent extraction or by other means. Thus, it is for example possible to subject the reaction mixture to fractional distillation. It is also possible to concentrate the reaction mixture, to take up the residue that remains in an organic solvent which is sparingly miscible with water, to treat the resulting solution with water and mineral acid and to separate the phases. Concentration of the organic phase affords the acylated (R)-amine. The (S)-amine can be isolated from the aqueous phase by initial treatment with base, subsequent extraction with an organic solvent which is sparingly miscible with water and drying and concentration of the combined organic phases. - If appropriate, the isolated products can be purified further, for example by chromatography or distillation.

The acylated (R)-amines of the formula

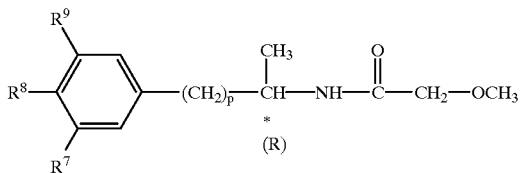

in which

R$^8$ represents fluorine, chlorine, bromine, methyl, methoxy or methylthio,

R$^7$ and R$^9$ each represent hydrogen and p represents the numbers 0, 1 or 2, or R$^8$ represents hydrogen, R$^7$ and R$^9$ each represent methyl and p represents 2, are novel.

Examples of acylated (R)-amines of the formula (IIIa) include the compounds of the following formulae:

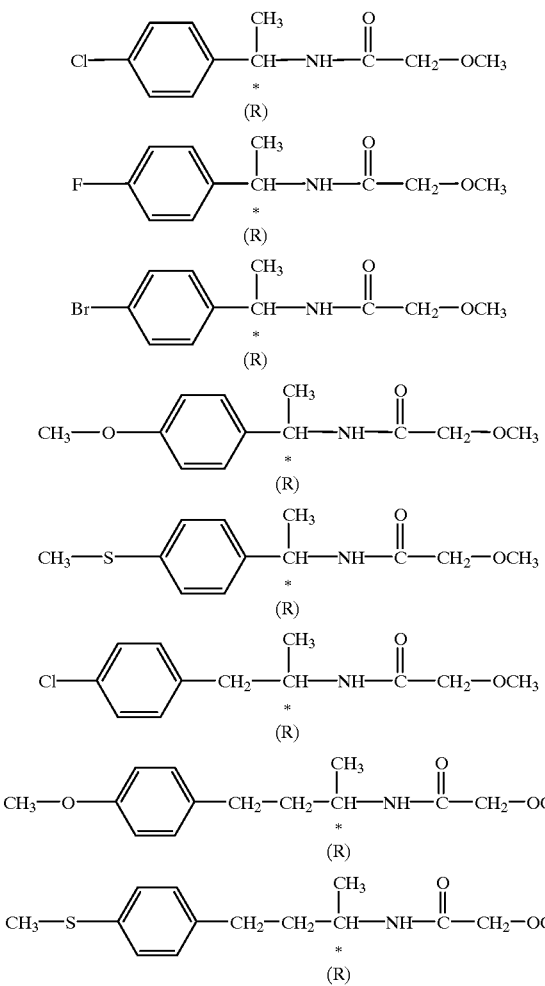

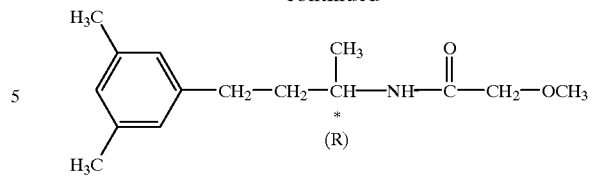

Suitable acids for carrying out the third step of the process according to the invention are all customary strong acids. Those which are preferably utilizable are mineral acids, such as sulphuric acid or hydrochloric acid.

Suitable bases for carrying out the third step of the process according to the invention are all customary strong bases. Those which are preferably utilizable are inorganic bases, such as sodium hydroxide or potassium hydroxide.

Suitable diluents for carrying out the third step of the process according to the invention are all organic solvents which are customary for such reactions, and water. Those which are preferably utilizable are water or mixtures of water and organic solvents, examples including mixtures of water and toluene.

When carrying out the third step of the process according to the invention, the temperatures may be varied within a relatively wide range. In general, the reaction is carried out at temperatures between 20 and 180° C., preferably between 30 and 150° C.

The third step of the process according to the invention is generally carried out under atmospheric pressure. However, it is also possible to work under elevated or reduced pressure When carrying out the third step of the process according to the invention, generally 1 to 5 equivalents or else a larger excess of acid or base are employed per mole of acylated (R)-amine of the formula (III). Work-up is carried out by customary methods. In general, after the cleavage has ended and after neutralization, the reaction mixture is extracted with an organic solvent which is sparingly miscible with water, and the combined organic phases are dried and concentrated. If appropriate, the resulting product can be freed from impurities which may still be present using customary methods.

The amines of the formula (I*) preparable by the process according to the invention are useful intermediates for preparing pharmaceuticals or active compounds having insecticidal, fungicidal or herbicidal properties (cf EP-A 0 519 211, EP-A 0 453 137, EP-A 0 283 879, EP-A 0 264 217 and EP-A 0 341 475). Thus, for example, the fungicidally active compound of the formula

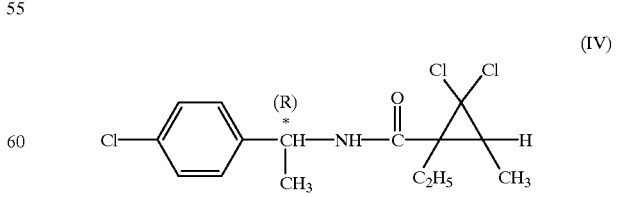

is obtained by reacting (R)-1-(4-chloro-phenyl)-ethylamine of the formula

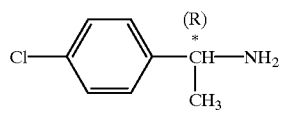

with 2,2-dichloro-1-ethyl-3-methyl-1-cyclopropanecarbonyl chloride of the formula

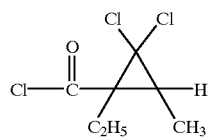

in the presence of an acid binder and in the presence of an inert organic diluent.

The examples that follow illustrate the practice of the process according to the invention.

PREPARATION EXAMPLES

Example 1

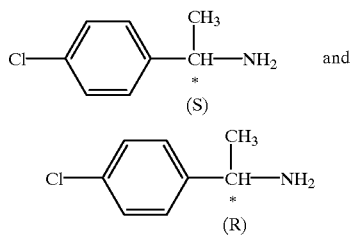

1st Step

At room temperature, a solution of 77.75 g (0.5 mol) of racemic 1-(4-chlorophenyl)-ethylamine in 260 g of methyl methoxyacetate is mixed with stirring with 3.9 g of Novozym 435™ (=immobilized lipase from Candida antarctica; 7300 U/g). The mixture is stirred at room temperature for a further 2.5 hours and the enzyme is then filtered off and rinsed with 20 g of methyl methoxyacetate.

2nd Step

The filtrate is concentrated under reduced pressure and the residue that remains is taken up in 300 ml of methylene chloride. The resulting solution is mixed with 100 ml of ice-water and 21 ml of concentrated hydrochloric acid and stirred at room temperature for 0.2 hours. The phases are then separated.

The organic phase is dried over magnesium sulphate and then concentrated under reduced pressure. In this manner, 61.9 g of a product are obtained which, according to gas chromatographic analysis, consists to 95% of the (R)-enantiomer of N-[1-(4-chlorophenyl)ethyl]-methyoxyacetamide. The ee value is 97.1%.

Thus, the calculated yield is 51.7% of theory.

With cooling, the aqueous phase obtained in the above phase separation is mixed with 35 ml of concentrated aqueous sodium hydroxide solution and then extracted three times with methylene chloride. The combined organic phases are dried over magnesium sulphate and then concentrated under reduced pressure. In this manner 37 g of a colourless liquid are obtained which, according to gas chromatographic analysis, consists to 98.2% of the (S)-enantiomer of 1-(4-chlorophenyl)ethylamine. The ee value is 91.8%.

Thus, the calculated yield is 46.6% of theory.

3rd Step

A mixture of 52 g (0.224 mol) of the resulting (R)-enantiomer of N-[1-(4-chloro-phenyl)-ethyl]-methoxyacetamide, 180 ml of water and 67.7 g of concentrated hydrochloric acid is heated under reflux for 10 hours. The reaction mixture is allowed to cool to room temperature, initially extracted once with methylene chloride, then made alkaline using concentrated aqueous sodium hydroxide solution and subsequently extracted three times with 200 ml of methylene chloride each time. The combined organic phases are dried over magnesium sulphate and then concentrated under reduced pressure. In this manner, 33.1 g of a product are obtained which, according to gas chromatographic analysis, consists to 99.1% of the (R)-enantiomer of 1-(4-chloro-phenyl)-ethylamine. The ee value is 95.1%.

The calculated total yield is 95% of theory.

Example 2

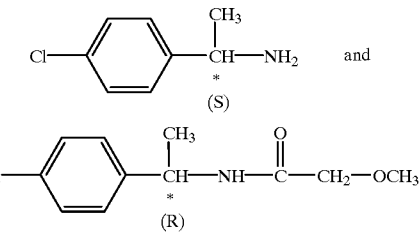

1st Step

At room temperature, a solution of 3.1 g (0.02 mol) of racemic 1-(4-chlorophenyl)-ethylamine in 20 ml of tert-amyl methyl ether is mixed with stirring with 10.4 g (0.1 mol) of methyl methoxyacetate and then 0.6 g of Novozym 435® (=immobilized lipase from Candida antarctica; 7300 U/g). Stirring is continued at 40° C. and the progress of the reaction is monitored by gas chromatographic sample analysis. After 1.5 hours, the conversion is 52%. At this stage, the reaction is terminated by filtering off the enzyme.

2nd Step

The filtrate that remains after the enzyme has been filtered off is subjected to fractional distillation.

In this manner, 1.3 g of a colourless liquid are obtained which, according to gas chromatographic analysis, consists to 94% of the (S)-enantiomer of 1-(4-chlorophenyl)-ethylamine. The ee value is >98%. Thus, the calculated yield is 43% of theory.

Additionally, 2.1 g of a product are obtained which, according to gas chromatographic analysis, consists to 99% of the (R)-enantiomer of N-[1-(4-chlorophenyl)-ethyl]-methoxyacetamide. The ee value is >98%. Thus, the calculated yield is 46.8% of theory.

Example 3

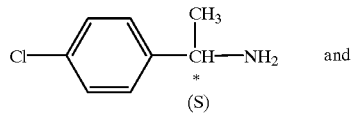

-continued

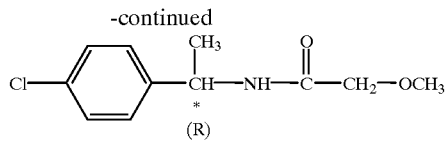

1st Step

At room temperature, a solution of 7.93 g (0.051 mol) of racemic 1-(4-chloro-phenyl)-ethylamine in 40 ml of methyl tert-butyl ether is mixed with stirring with 13.2 g (0.1 mol) of n-propyl methoxyacetate and then with 0.45 g of Novozym 435® (=immobilized lipase from Candida antarctica; 7300 U/g). Stirring is continued at 40° C. and the progress of the reaction is monitored by gas chromatographic sample analysis.

After 1.5 hours, the conversion is 52%. At this stage, the reaction is terminated by filtering off the enzyme.

2nd Step

The filtrate that remains after the enzyme has been filtered off is subjected to fractional distillation.

In this manner, 3.5 g (44.3% of theory of the (S)-enantiomer of 1-(4-chloro-phenyl)-ethylamine are obtained. The ee value is 96.4%.

Additionally, 5.2 g (45.1% of theory) of the (R)-enantiomer of N-[1-(4-chloro-phenyl)-ethyl]-methoxyacetamide are obtained. The ee value is 99%.

Example 4

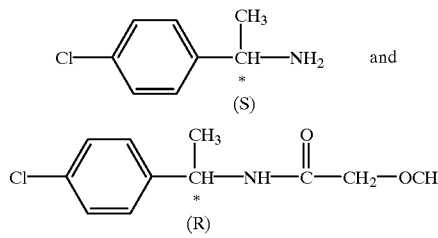

1st Step

At room temperature, a solution of 7.8 g (0.05 mol) of racemic 1-(4-chloro-phenyl)-ethylamine in 35 ml of methyl tert-butyl ether is mixed with stirring with 8.32 g (0.08 mol) of methyl methoxyacetate and then with 0.39 g of Novozym 435® (=immobilized lipase from Candida antarctica; 7300 U/g). Stirring is continued at room temperature and the progress of the reaction is monitored by gas chromatographic sample analysis. After 4.5 hours, the conversion is 55%. At this stage, the reaction is terminated by filtering off the enzyme. In the filtrate that remains, the (S)-enantiomer of 1-(4-chloro-phenyl)-ethylamine has an ee value of 98.1%, while the (R)-enantiomer of N-(1-(4-chlorophenyl)-ethyl]-methoxyacetamide obtained has an ee value of 96%.

Example 5

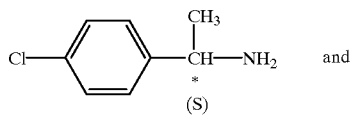

-continued

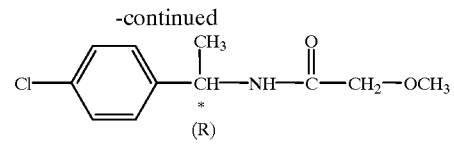

1st Step

At room temperature, a solution of 7.8 g (0.05 mol) of racemic 1-(4-chloro-phenyl)-ethylamine in 40 ml of methyl tert-butyl ether is mixed with stirring with 13.2 g (0.13 mol) of methyl methoxyacetate and then with 80 mg of Novozym 435® (=immobilized lipase from Candida antarctica; 7300 U/g). Stirring is continued at 40° C. and the progress of the reaction is monitored by gas chromatographic sample analysis. After 3 hours, the conversion is 43.8%. At this stage, the reaction is terminated by filtering off the enzyme. In the filtrate that remains, the (R)-enantiomer of N-[1-(4-chlorophenyl)-ethyl]-methoxyacetamide has an ee value of 97.7%.

Example 6

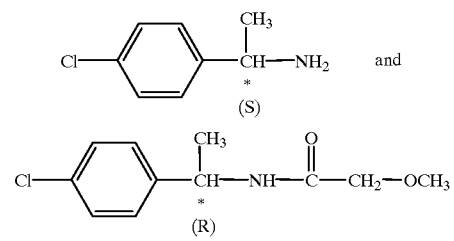

1st Step

At room temperature, a solution of 7.8 g (0.05 mol) of racemic 1-(4-chloro-phenyl)-ethylamine in 40 ml of methyl tert-butyl ether is mixed with stirring with 10.4 g (0.1 mol) of methyl methoxyacetate and then with 0.45 g of Novozym 435® (=immobilized lipase from Candida antarctica; 7300 U/g). Stirring is continued at 60° C. and the progress of the reaction is monitored by gas chromatographic sample analysis. After 3 hours, the conversion is 54%. At this stage, the reaction is terminated by filtering off the enzyme. In the filtrate that remains, the (S)-enantiomer of 1-(4-chlorophenyl)-ethylamine has an ee value of 98.8%, while the (R)-enantiomer of N-(1-(4-chlorophenyl)-ethyl]-methoxyacetamide obtained has an ee value of 94.4%.

Example 7

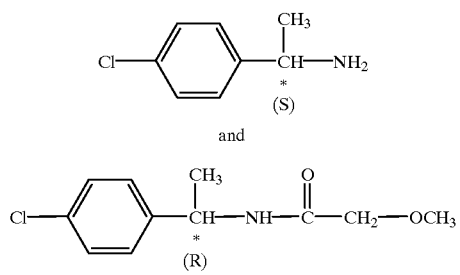

1st Step

At room temperature, a solution of 16.6 g (0.107 mol) of racemic 1-(4-chloro-phenyl)-ethylamine in 41 g of methyl methoxyacetate is mixed with stirring with 1.2 g of Novozym 435® (=immobilized lipase from Candida antarctica; 7300 U/g). Stirring is continued at 40° C. and the progress of the reaction is monitored by gas chromatographic sample analysis. After 2.5 hours, the conversion is 54%. At this stage, the reaction is terminated by filtering off the enzyme. In the filtrate that remains, the (S)-enantiomer of 1-(4-chloro-phenyl)-ethylamine has an ee value of 95.6%, while the (R)-enantiomer of N-(1-(4-chlorophenyl)-ethyl]-methoxyacetamide obtained has an ee value of 95.3%.

Example 8

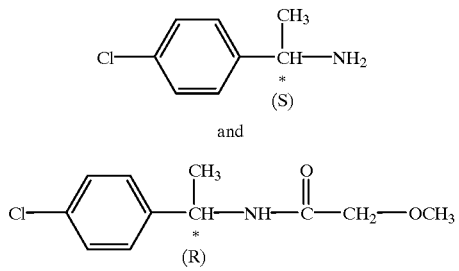

1st Step

At room temperature, a solution of 20.06 g (0.129 mol) of racemic 1-(4-chloro-phenyl)-ethylamine in 20 g (0.19 mol) of methyl methoxyacetate is mixed with stirring with 1 g of Novozym 435® (=immobilized lipase from Candida antarctica; 7300 U/g). Stirring is continued at room temperature for one hour and the reaction is then terminated by filtering off the enzyme. The conversion is 43.9%. In the filtrate that remains, the (S)-enantiomer of 1-(4-chloro-phenyl)-ethylamine has an ee value of 61%, while the (R)-enantiomer of N-[1-(4-chlorophenyl)-ethyl]-methoxyacetamide obtained has an ee value of 98.4%.

Example 9

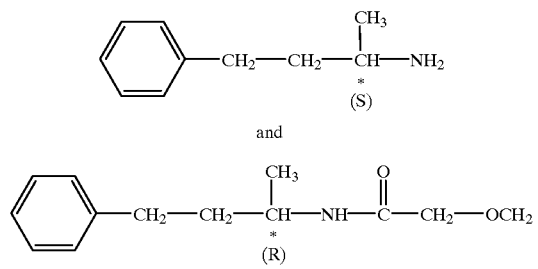

1st Step

At room temperature, a solution of 11.92 g (0.08 mol) of racemic 3-phenyl-1-methyl-propylamine in 34 ml of methyl tert-butyl ether is mixed with 8.32 g (0.08 mol) of methyl methoxyacetate and with 0.47 g of Novozym 435® (=immobilized lipase from Candida antarctica; 7300 U/g) and then stirred at 35 to 40° C. The progress of the reaction is monitored by taking samples which are analysed by gas chromatography. After only 0.5 hours, the conversion is 41%. After a total of 3 hours, the reaction is terminated by filtering off the enzyme. The conversion is 53.8%.

2nd Step

The filtrate that remains after filtering off the enzyme is subjected to fractional distillation.

In this manner, 5.15 g of the (S)-enantiomer of 3-phenyl-1-methyl-propylamine having an ee value of 89.7% are obtained. The calculated yield is thus 43.2% of theory.

Additionally, 7.88 g of the (R)-enantiomer of N-(3-phenyl-1-methyl-propyl)- methoxyacetamide having an ee value of 94% are obtained. The calculated yield is thus 46.7% of theory.

Example 10

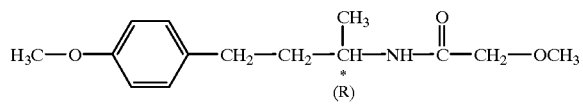

A mixture of 17.9 g (0.1 mol) of racemic 1-methyl-3-(4-methoxy-phenyl)-propylamine, 10.4 g (0.1 mol) of methyl methoxyacetate, 0.75 g of Novozym 435® (immobilized lipase from Candida antarctica) and 80 ml of methyl tert-butyl ether is stirred at 40° C. for 3 hours. The enzyme is then filtered off. The solution that remains is mixed with 100 ml of 10% strength aqueous hydrochloric acid and then concentrated under reduced pressure. The residue is cooled to 0° C. and the resulting solid is filtered off and dried. In this manner, 9.95 g of a product are obtained which, according to the gas chromatogram, consists of 99.2% of the (R)-enantiomer of N-[[3-(4-methoxy-phenyl)-1-methyl]-propyl]-methoxyacetamide. The calculated yield is thus 39.6% of theory. The ee value is 99%.

$^1$H NMR spectrum/CDCl$_3$/TMS):

δ=1.1 (d, 3H, CH$_3$); 1.63–1.71 (m, 2H, CH$_2$); 2.48–2.58 (m, 2H, CH$_2$); 3.32 (s, 3H, CH$_3$); 3.69 (s, 3H, CH$_3$); 3.78 (d, 2H, CH$_2$); 4.0 (m, H, CH); 6.3 (d, 1H, NH); 6.7–7.03 (m, 4H, aromat. H) ppm Example 11

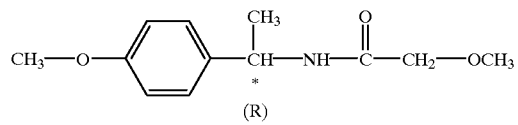

A mixture of 51.3 g (0.34 mol) of racemic 1-(4-methoxy-phenyl)ethylamine, 35.3 g (0.34 mol) of methyl methoxyacetate, 2.5 g of Novozym 435® (=immobilized lipase from Candida antarctica) and 80 ml of methyl tert-butyl ether is stirred at 40° C. for 5 hours. The enzyme is then filtered off. The solution that remains is mixed with 100 ml of 10% strength aqueous hydrochloric acid and then concentrated under reduced pressure. The residue is cooled to 0° C. and the resulting solid is filtered off and dried. In this manner, 38.5 g of a product are obtained which, according to, the gas chromatogram, consists to 96% of the (R)-enantiomer of N-[1-(4-methoxy-phenyl)-ethyl]-methoxyacetamide. The calculated yield is thus 40.2% of theory. The ee value is 98.3%.

$^1$H NMR spectrum/CDCl$_3$/TMS):

δ=1.49 (d, 3H, CH$_3$); 3.38 (s, 3H, CH$_3$); 3.79 (s, 3H, CH$_3$); 3.87 (d, 2H, CH$_2$); 5.13 (m, 1H, CH); 6.68 (d, 1H, NH); 6.9–7.28 (m, 4H, aromat. H) ppm.

What is claimed is:

1. A process for preparing an optically active amine of the formula:

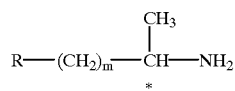
(I*)

in which
R represents a substituted phenyl group of the formula:

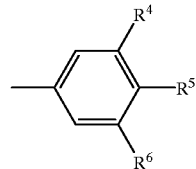

in which
$R^4$ and $R^6$ are hydrogen and $R^5$ is chlorine, fluorine, methyl or methoxy, and
m represents the numbers 0, 1 or 2, which process comprises
a) reacting in a first step a racemic amine of the formula:

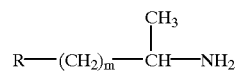
(I)

in which
R and m are each defined as above,
with an ester of the formula

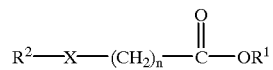
(II)

in which
$R^1$ represents methyl, ethyl, n-propyl, n-butyl, chloromethyl, 2-chloroethyl, 2-fluoroethyl or 2,2,2-trifluoroethyl,
R2 represents hydrogen
X represents oxygen, and
n represents the numbers 1 or 2, in the presence of 10,000 to 112,000 units per mole of racemic amine of lipase from *Candida antarctica* and, in the presence of a diluent,
b) separating in a second step the resulting mixture of (S)-amine of the formula:

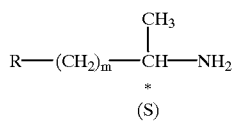
(I-S)
(S)

in which
R and m are each as defined above,

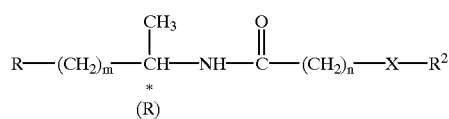
(III)
(R)

and acylated (R)-amine of the formula:
in which
R, $R^2$, X, m and n are each defined above, and
c) setting free, in a third step, the (R)-amine of the formula:

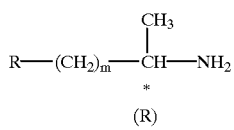
(I-R)
(R)

in which
R and m are each as defined above, by treatment of the acylated (R)-amine of the formula (III) with an acid or base in the presence of a diluent.

2. The process according to claim 1, wherein the racemic amine of formula (I) is 1-(4-chlorophenyl)-ethylamine of the formula

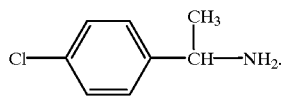

3. The process according to claim 1 wherein the ester of formula (II) is methyl methoxyacetate of the formula

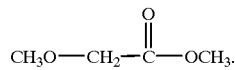

4. The process according to claim 1, wherein the first step is carried out at temperatures between 0° C. and 80° C.

* * * * *